United States Patent [19]

von Deessen et al.

[11] Patent Number: 5,126,500
[45] Date of Patent: Jun. 30, 1992

[54] PREPARATION OF RETINYL GLYCOSIDES AND INTERMEDIATES THEREFOR

[75] Inventors: Ulrich von Deessen, Speyer; Joachim Paust, Neuhofen; Klaus Kaiser, Neustadt; Helmut Indest, Weinheim, all of Fed. Rep. of Germany

[73] Assignee: BASF Aktiengesellschaft, Ludwigshafen, Fed. Rep. of Germany

[21] Appl. No.: 646,707

[22] Filed: Jan. 28, 1991

[30] Foreign Application Priority Data

Feb. 2, 1990 [DE] Fed. Rep. of Germany ........ 4003094

[51] Int. Cl.$^5$ .................. C09D 309/10; A61K 31/70; C07H 15/00; C07H 15/18
[52] U.S. Cl. ..................... 536/4.1; 536/119; 536/18.1; 549/417
[58] Field of Search ............... 514/58, 25, 35; 536/4.1, 18.1, 119; 424/180; 549/417

[56] References Cited

U.S. PATENT DOCUMENTS

| 4,457,918 | 7/1984 | Holick et al. | 514/25 |
| 4,855,463 | 8/1989 | Barva et al. | 536/119 |

OTHER PUBLICATIONS

Angew. Chem. 94 (1982) 184–201.
Xenobiotica 17 (1987) 1451–1471.
Biochem. J. 244 (1987) 231–234.
H. Hulburch, Kontakte Mar. 1979, pp. 14 50 23.
J. Org. Chem. 26 (1961) 908–911.
Methods in Carbohydrate Chemistry, vol. II (1963) 221–228, Academic Press Whistler, Wolfrom.
John F. Kennedy, Carbohydrate Chemistry, Clarendon Press, 1988, pp. 500–552.
T. W. Greene, Protective Groups in Organic Synthesis, John Wiley & Sons, 1981.
H. Pommer, P. C. Thieme, Topics in Current Chemistry 109 (1985) 165–188.
E. V. Dehmlow, Angewandte Chemie 89 (1977) 521 et seq and 86 (1974) 187 et seq.

Primary Examiner—Ronald W. Griffin
Assistant Examiner—Louise Leary
Attorney, Agent, or Firm—Keil & Weinkauf

[57] ABSTRACT

A process for preparing retinyl glycosides of the formula I

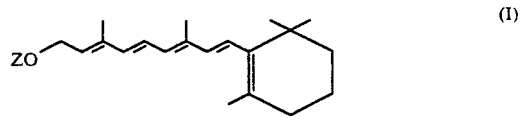
(I)

where Z is a glycosidic residue, by glycosidation of a completely acylated carbohydrate or completely acylated glycosidic polymer of the formula II Z (acylated)-Y (II)

where Y is a leaving group customary for glycosidations in the 1-position of the glycoside, comprises the acylated glycoside being reacted with an aldehyde-protected 4-hydroxy-2-methyl-2-buten-1-al under the conditions customary for glycosidations, eliminating the aldehyde protective group from the resulting compound, subjecting the resulting aldehyde to a Wittig reaction with a β-ionylideneethyltriphenylphosphonium salt and eliminating the acyl groups on the resulting retinyl glycoside in a conventional manner.

The process according to the invention is particularly important for preparing retinyl glycosides of the formula Ia

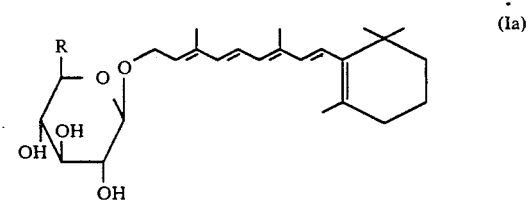
(Ia)

where R is —CH$_2$—OH, —COOH or —COOCH$_3$.
Intermediates of this process are also claimed.

8 Claims, No Drawings

PREPARATION OF RETINYL GLYCOSIDES AND INTERMEDIATES THEREFOR

The present invention relates to a process for preparing retinyl glycosides, especially retinyl glucuronides and retinyl β-D-glucopyranoside, and to novel intermediates for this process.

Carbohydrates, especially the glycosides, are particularly important for cell-cell interactions. They act as receptors for hormones, proteins, bacteria and viruses. In addition, they determine the antigenic properties of cells (cf. for example H. Paulsen, Angew. Chem. 94 (1982) 184–201).

Interest in glucuronides in particular has greatly increased in recent years since it was found that. these substances have unusual biological activities (see, for example, F. M. Kaspersen et al. in Xenobiotica 17 (1987) 1451–1471).

Thus, for example, retinyl glucuronides promote the growth of rats, inhibit tumor cells and are involved in cell differentiation (cf. J. A. Olson in Chemica Scripta 27 (1987) 179–183 and A. B. Barua et al. in Biochem. J. 252 (1988) 415–420).

To date essentially 2 processes have been disclosed for preparing retinyl glucuronides. As reported by Barua et al. in Biochem. J. 244 (1987) 231–234, methyl retinylglucuronate is obtained by reacting all-trans-retinol with methyl 2,3,4-tri-O-acetyl-1-bromo-1-deoxy-β-D-glucopyranuronate in diethyl ether in the presence of $Ag_2CO_3$ and subsequent hydrolysis. The disadvantage of this process is that the yields which can be achieved are only about 15% of theory.

In the process of U.S. Pat. No. 4,457,918, glycosides of vitamins A, E and K are obtained by reacting the relevant vitamins with an acylated carbohydrate or an acylated glycosidic polymer, which has a suitable leaving group in the 1-position of the carbohydrate or the terminal glycosidic residue, in an inert non-polar solvent in the presence of silver trifluoromethanesulfonate and 2,4,6-trimethylpyridine, with subsequent basic deacylation of the glycosidic residues. The yields obtained with this process are also unsatisfactory. Another disadvantage of this process is that the great sensitivity of retinol to acids greatly restricts the choice of glycosidation catalyst and of protective groups in the carbohydrate moiety.

It is an object of the present invention to develop a process which can be used to prepare in a very straightforward manner glycosides of retinol (vitamin A) in good yields.

We have found that this object is achieved by initially forming a glycosidic linkage between an aldehyde-protected 4-hydroxy-2-methyl-2-buten-1-al and an acylated sugar unit and subsequently eliminating the aldehyde protective group and subjecting the resulting formyl group to a Wittig reaction with a β-ionylideneethyltriphenylphosphonium salt.

Hence the present invention relates to a process for preparing retinyl glycosides of the formula I

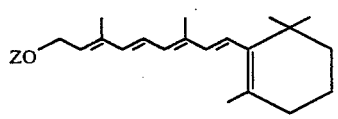

(I)

where Z is a straight-chain or branched glycosidic residue containing from 1 to 20, preferably 1 to 3, in particular 1 to 2, glycosidic units per residue, by glycosidation of a completely acylated carbohydrate or completely acylated glycosidic polymer of the formula II $$Z_{(acylated)}\text{-}Y \qquad (II)$$

where Y is a leaving group customary for glycosidations, such as F, Cl, Br

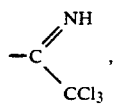

preferably Cl or Br, in the 1-position of the carbohydrate or in the 1-position of the terminal glycoside unit, and where the H atoms of the free OH groups of the acylated glycoside or acylated glycosidic polymer have been replaced by $-CO-R_1$ where $R_1$ is alkyl of 1 to 10 carbon atoms, preferably 1 or 2 carbon atoms, or aralkyl, preferably benzyl, which comprises A. reacting the acylated carbohydrate or glycosidic polymer with an aldehyde-protected 4-hydroxy-2-methyl-2-buten-1-al of the formula III

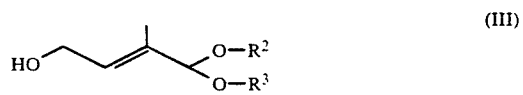

(III)

where $R^2$ and $R^3$ are each alkyl of 1 to 10, preferably 1 to 4, carbon atoms, especially methyl or ethyl, or aralkyl of 7 to 10 carbon atoms or phenyl, or $R^2$ and $R^3$ are together ethylene or propylene, each of which can be substituted by alkyl groups of 1 to 4 carbon atoms, preferably one or more methyl groups, especially 2,2-dimethylpropylene, under the conditions customary for glycosidations, B. eliminating the aldehyde protective group from the resulting compound of the formula IV

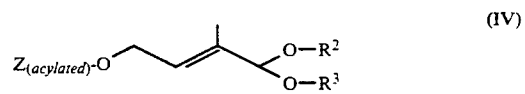

(IV)

with acid,

C. subjecting the resulting aldehyde of the formula V

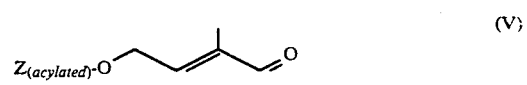

(V)

to a Wittig reaction with a β-ionylideneethyltriphenylphosphonium salt of the formula VI

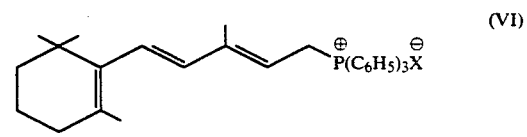

(VI)

where X is a singly charged anion, especially Cl, Br or $HSO_4$, and

D. eliminating the acyl groups of the glycoside residue in the resulting acylated retinyl glycoside of the formula VII

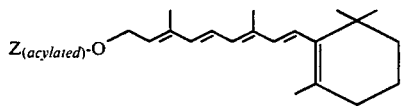
(VII)

in a conventional manner.

The process according to the invention is particularly important for preparing retinyl glycosides of the formula Ia (Ia)

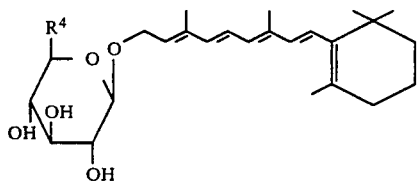

where $R^4$ is —$CH_2$—OH, —COOH or —$COOCH_3$, by
A. reacting an acylated glycoside of the formula II

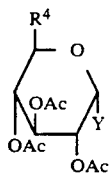
(II)

where $R^4$ is —$CH_2$—$OCOCH_3$ or —$COOCH_3$, Y is F, Cl, Br or

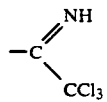

especially Br, and Ac is acyl of 1 to 11 carbon atoms, preferably acetyl, or arylcarbonyl, preferably benzoyl, with an aldehyde-protected 4-hydroxy-2-methyl-2-buten-1-al of the formula III, B. eliminating the aldehyde protective group from the resulting compound of the formula IVa

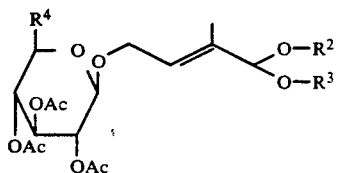
(IVa)

where $R^2$, $R^3$ and Ac have the abovementioned meanings, and $R^4$ is —$CH_2$—$OCOCH_3$ or —$COOCH_3$, C. reacting the resulting aldehyde of the formula Va

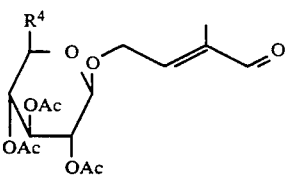
(Va)

with a $\beta$-ionylideneethyltriphenylphosphonium salt of the formula VI and

D. eliminating the protective groups in the glycosidic residue of the resulting retinyl glycoside of the formula VIIa

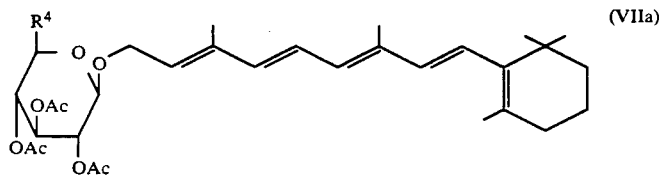
(VIIa)

in a conventional manner and, if desired, fractionating the racemic compound VIIa into its cis and trans isomers.

The present invention also relates to intermediates which make the extremely advantageous process according to the invention possible at all. The following may be mentioned 1-O-(2'-methyl-2'-buten-4'-yl-1'-al-neopentyl-glycolacetal)-2,3,4,6-tetra-O-acetyl-$\beta$-D-glucopyranoside and methyl [1-O-(2'-methyl-2'-buten-4'-yl-1'-al-neopentylglycolacetal)-2,3,4-tri-O-acetyl-$\beta$-D-glucopyranoside]uronate (both compounds of the formula IVa where $R^2$ and $R^3$ together are —$CH_2$—$C(CH_3)_2$—$CH_2$—, Ac is acetyl and $R^3$ is —$CH_2$—O—CO—$CH_3$ or —$COOCH_3$) and 1-O-(2'-methyl-2'-buten-4'-yl-1'-al)-2,3,4,6-tetra-O-acetyl-$\beta$-D-glucopyranoside and methyl [1-O-(2'-methyl-2'-buten-4'-yl-1'-al)-2,3,4-tri-O-acetyl-$\beta$-D-glucopyranoside]-uronate (both compounds of the formula Va where Ac is acetyl and $R^3$ is —$CH_2$—O—CO—$CH_3$ or —$COOCH_3$).

The present invention also relates to the use of the intermediates of the formulae IV, IVa, V and Va for preparing drugs. For details of the preparation and use of drugs prepared from retinyl glycosides, reference may be made to, for example, F. M. Kaspersen, Xenobiotica 17 (1987) 1451–71 and G. A. Pitt, Biochem. Soc. Trans. 14 (1986) 923–984.

The term glycosidic units means both glycopyranosyl and glycofuranosyl units, as well as the amino derivatives or uronic acids thereof. In what are called glycosidic polymers, one or more of the O—$COR^1$ groups in the carbohydrate ring is replaced by a completely acylated glycosidic unit, with the proviso that the number of glycosidic units does not exceed 20. The sequence of the glycosidic units in the polymer has no influence on the process according to the invention.

The terms carbohydrate and glycosidic polymer are used for the purposes of the present invention to mean monosaccharides, i.e. pentoses and hexoses in the pyranose or furanose form, such as, in particular, glucose, mannose and galactose; disaccharides such as lactose, maltose, gentiobiose, sucrose and cellobiose; polysaccharides such as maltotriose, maltodextrin and glucans, aminohexoses such as glucosamine, galactosamine or mannosamine, and hexuronic acids such as glucuronic, galacturonic, mannuronic or 2-keto-L-gulonic acid.

Before the glycosidation, the functional groups of the glycosides or glycosidic polymers must be protected. Suitable protective groups are those which can be easily eliminated again with bases Particularly important for protecting the free OH groups are acetyl, propionyl and benzoyl Suitable protective groups for the COOH groups of the uronic acids are, in particular, methyl, ethyl and benzyl (cf. H. Hulbuch, Kontakte 3/79, pages 14 to 23).

Suitable protective groups for the amino groups of the aminohexoses are, in particular, organic acyl. radicals of 2 to 10 carbon atoms, such as acetyl, propionyl or butyryl, especially acetyl.

Leaving groups customarily used for glycosidations are: F, Cl, Br and

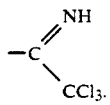

Particularly important leaving groups are the halogens, especially Cl and Br. The acylated glycosides containing a suitable leaving group in the 1-position of the first (or only) glycosidic ring are obtained, for example, by the methods described in Methods in Carbohydrate Chemistry, Vol. II (1963) 221-222 and 228 et seq. or in J. Org. Chem. 26 (1961) 908–911.

The aldehyde-protected 4-hydroxy-2-methyl-2-buten-1-al of the formula III which is particularly employed according to the invention is the neopentyl glycol acetal thereof.

The glycosidation with the alcohols of the formula III is straightforward and can therefore be carried out by all the methods customary in carbohydrate chemistry. Details of glycosidation methods are to be found in the following literature, which is incorporated herein by reference: Whistler, Wolfrom, "Methods in Carbohydrate Chemistry", Academic Press, Vol. II (1963) 326-366, Vol. VIII (1980) 233-261, and John F. Kennedy, "Carbohydrate Chemistry", Clarendon Press, 1988, 500-552.

It is particularly advantageous to carry out the glycosidation in the presence of silver salts, $Hg(CN)_2$ or $HgBr_2$, Lewis acids such as $BF_3$, $SnCl_4$ or $TiCl_4$ in aprotic solvents such as dimethylformamide (DMF), hexane, methylene chloride, toluene, petroleum ether or dichloroethane The reaction temperature is generally from $-40°$ to $100°$ C., preferably $-20°$ C. to room temperature. The progress of the reaction can be followed by thin-layer chromatography. The reaction product can be purified by column chromatography on silica gel or by crystallization from alkanols, especially methanol.

The aldehyde protective group is eliminated in a conventional manner. For example, acetals are cleaved by heating in the presence of acid catalysts. (See, for example, T. W. Greene, Protective Groups in Organic Synthesis, John Wiley & Sons, 1981).

The Wittig reaction is carried out by adding a strong base such as NaOH, KOH or $NH_3$ to approximately equimolar amounts of the glycoside aldehyde of the formula V or Va and of the β-ionylideneethyltriphenylphosphonium salt in a mixture of a non-polar solvent customary for Wittig reactions, such as methylene chloride, benzene, toluene, chloroform, 1,2-dichloroethane, hexane, cyclohexane or petroleum ether, and water at from about $-20°$ to $+100°$ C., preferably $-5$ to room temperature, while stirring vigorously. It has proven advantageous in some cases to carry out the Wittig reaction in the presence of a phase-transfer catalyst.

Suitable phase-transfer catalysts are, in particular: tetraalkylammonium salts of the formula VIII

where the R radicals can be identical or different and each can be alkyl of 1 to 22 carbon atoms or alkyl of up to 25 carbon atoms which contains functional groups such as hydroxyl, acylamino or alkoxy groups, such as methyl, ethyl, (iso)propyl, butyl, octyl, dodecyl, $C_{16}H_{33}$—, hydroxy(iso)propyl or

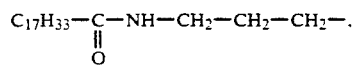

and phenyl or phenyl-substituted alkyl (such as benzyl) of up to 20 carbon atoms, and $X^\ominus$ is an anion such as $I^-$, $Cl^-$, $Br^-$, $HSO_4^-$, $CN^-$ or $BF_4^-$; in particular trimethylbenzylammonium chloride which is very reasonably priced and can be used in the form of a 50% strength aqueous solution, and tricaprylmethylammonium chloride; and tetraalkylphosphonium salts of the formula IX

where R and $X^\ominus$ have the meanings stated for formula VIII, especially tri-n-octylmethylphosphonium iodide.

The phase-transfer catalysts are employed in amounts of from 0.01 to 1, preferably 0.1 to 0.5, mole per mole of aldehyde.

For further details of Wittig reactions, reference may be made to H. Pommer, P. C. Thieme, Topics in Current Chemistry 109 (1985) 165–188, and for further details of phase-transfer catalysts, reference may be made to E. V. Dehmlow, Angewandte Chemie 89 (1977) 521 et seq. and loc. cit. 86 (1974) 187 et seq.

The elimination of the protective groups from the resulting acylated retinyl glycoside of the formula VII or VIIa can be carried out in a conventional manner, for example by treatment with bases such as sodium methylate in methanol, ammonia in methanol or a strongly basic ion exchanger such as Amberlyst ® A-26 (OH form) in methanol.

The retinyl glycosides obtained according to the invention are racemates. These can subsequently be resolved into the cis and trans isomers by, for example, column chromatography on silica gel. This racemate resolution can be carried out before or after the elimination of the protective groups from the retinyl glycoside. It is particularly advantageous to carry out the racemate resolution before elimination of the protective groups.

The working up of the reaction mixture and the purification of the reaction products are carried out in a conventional manner, for example by filtration and concentration of the filtrate and, where appropriate, chromatography.

The process according to the invention can be used to prepare the retinyl glycosides of the formulae I and, in particular, Ia in significantly higher yields than in the prior art. The process according to the invention takes place by a synthetic route via novel interesting intermediates.

EXAMPLE 1

A. Preparation of 1-O-(2'-methyl-2'-buten-1'-al-neopentylglycolacetal-4'-yl)-2,3,4,6-tetra-O-acetyl-β-D-glucopyranoside

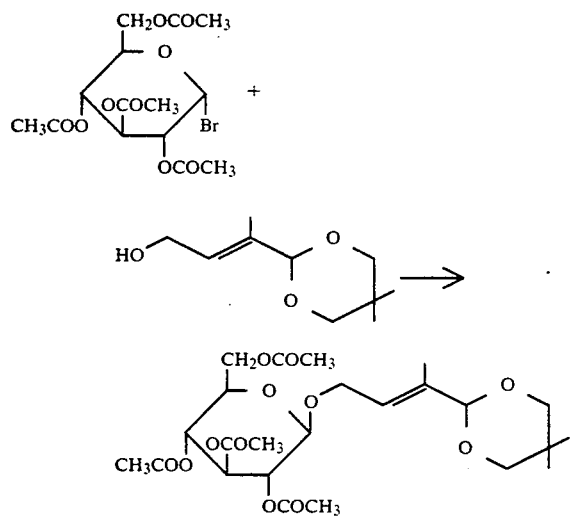

10.0 g (53.7 mmol) of 4-hydroxy-2-methyl-2-buten-1-al neopentyl glycol acetal, 5 g of molecular sieves (4Å, powdered) and 10 g (36.3 mmol) of silver carbonate were taken up in 10 ml of absolute (abs.) methylene chloride, and the mixture was stirred at room temperature (RT) under an argon atmosphere for 15 minutes (min). Then a solution of 14.7 g (35.8 mmol) of tetraacetylglucosyl bromide in 10 ml of CH$_2$Cl$_2$ was added dropwise over the course of 30 min. The mixture was then stirred until reaction was complete, which took about 12 h. The progress of the reaction was followed by thin-layer chromatography (TLC) on silica gel plates with CHCl$_3$/ethyl acetate (EA) in the ratio 2:1 by volume (V/V). After the reaction was complete, the mixture was diluted with CH$_2$Cl$_2$, filtered through a membrane filter and then concentrated under reduced pressure to a syrup. The product was purified by column chromatography (adsorbent: silica gel 60 from Merck, toluene/methanol 10:1 V/V). The product can also be crystallized from ethanol (about 3 ml/g). Yield: 16.0 g:86.5% of theory.

$[\alpha]_D^{20}$: $-20.1°$ (C=1; CHCl$_3$).

Melting point: 98.5° to 104.9° C.

B. Preparation of 1-O-(2'-methyl-2'-buten-4'-yl-1'-al)-2,3,4,6-tetra-O-acetyl-β-D-glucopyranoside 9.0 g (17.8 mmol) of the glucopyranoside prepared as in A. were taken up in 25 ml of a 60% by weight aqueous solution of acetic acid and heated to 40° C. Dissolution was complete after 15 min. According to TLC (adsorbent: silica gel 60, Merck, CHCl$_3$/EA 1:1 V/V) the reaction was complete after a further 30 min. The mixture was then concentrated under reduced pressure at a bath temperature not exceeding 40° C., and the remaining acetic acid was removed by distillation with toluene several times. The resulting syrupy residue was taken up in 20 ml of ethanol, and the product was induced to crystallize. Yield: 6.9 g corresponding to 92% of theory.

$[\alpha]_D^{20}$: $-18.5°$ (C=1; CHCl$_3$).

Melting point: 102° to 105° C.

C. Preparation of retinyl 2,3,4,6-tetra-O-acetyl-β-D-glucopyranoside 5 g (11.6 mmol) of the 1-O-(2'-methyl-2'-buten-4'-yl-1'-al)-2,3,4,6-tetra-O-acetyl-β-D-glucopyranoside obtained as in B. and 6.5 g (11.6 mmol) of β-ionylideneethyltriphenylphosphonium chloride were dissolved under an N$_2$ atmosphere in 100 ml of methylene chloride, and 75 ml of water were added. The mixture was then cooled to 0° C., 25 ml of a 1N aqueous NaOH solution were added, and the mixture was stirred vigorously with a turbine-type impeller. The reaction was complete after about 30 min (TLC: toluene/EA 3:1 V/V). The organic phase was separated off, washed with water, dried over MgSO$_4$ and concentrated under reduced pressure. Fractionation on silica gel (silica gel 60, Merck, toluene/EA 4:1) produced the desired compound as a cis/trans mixture in a yield of 5.57 g, corresponding to 76% of theory.

The mixture was then fractionated by column chromatography (adsorbent: silica gel 60, toluene/EA 7:1 V/V). This yielded 1. the cis isomer with $[\alpha]_D^{20}$: $-26.3°$ (C=1; CHCl$_3$)
2. the trans isomer with $[\alpha]_D^{20}$: $-31.6°$ (C=1; CHCl$_3$)

D. Preparation of retinyl β-D-glucopyranoside a. cis isomer 250 mg (0.4 mmol) of the cis-tetraacetyl isomer obtained as in C. were dissolved in 4 ml of methanol and, at RT, 0.2 ml of a 0.1N NaOCH$_3$ solution was added. After about 1.5 h (TLC check, CHCl$_3$/methanol 10:1 V/V) the mixture was neutralized with Lewatit CNP L F (H⊕) and concentrated under reduced pressure.

Yield: 179 mg, corresponding to 98% of theory $[\alpha]_D^{20}$: $-21.4°$ (C=1.5; methanol).

b. trans compound 192 mg (0.3 mmol) of the trans-tetraacetyl isomer obtained as in C. were reacted in a similar manner to Example 1D.a. The desired trans-retinyl β-D-glucopyranoside was obtained in a yield of 136 mg, corresponding to 98% of theory.

$[\alpha]_D^{20}$: $-43.0°$ (c=2; methanol).

EXAMPLE 2

A. Preparation of methyl [1-O-(2'-methyl-2'-buten-1'-al-neopentylglycolacetyl-4'-yl)-2,3,4-tri-O-acetyl-β-D-glucopyranosid]-uronate 2.8 g (15.0 mmol) of 4-hydroxy-2-methyl-2-buten-1-al neopentyl glycol acetal, 5 g of molecular sieves (4Å, powdered) and 3 g (10.9 mmol) of silver carbonate were taken up in 10 ml of abs. CH$_2$Cl$_2$, and the mixture was stirred under a nitrogen atmosphere at RT for 15 min.

Then a solution of 3.0 g (7.55 mol) of methyl 1-bromo-D-glucuronate in 6 ml of $CH_2Cl_2$ added dropwise over the course of 30 min. Reaction was complete after about 12 h. The mixture was diluted with 50 ml of $CH_2Cl_2$, filtered through a membrane filter and then concentrated under reduced pressure. The product was purified by column chromatography (adsorbent: silica gel 60, $CHCl_3$/EA 9:1 V/V). Crystallization from methanol is also possible for purification.

Yield: 3.6 g, 94% of theory.
$[\alpha]_D^{20}$: $-32.8°$ (C=1; $CHCl_3$).
Melting point: 107° C.

B. Preparation of methyl [1-O-(2'-methyl-2'-buten-4'-yl-1-al)-2,3,4'-tri-O-acetyl-β-D-glucopyranosid]-uronate 10.0 g (19.9 mmol) of a uronate prepared as in Example 2A were taken up in 30 ml of a 60% strength aqueous solution of acetic acid and heated to 40° C. A clear solution was obtained after about 10 min and the reaction was complete after a further 30 min. (TLC; $CHCl_3$/EA 2:1 V/V). The mixture was concentrated under reduced pressure and distilled with toluene several times in order to remove the acetic acid completely. The remaining pale yellow oil was taken up in ethanol, and the resulting aldehyde was induced to crystallize.

Yield: 7.2 g. corresponding to 87% of theory
$[\alpha]_D^{20}$: $-31.8°$ (C=1; $CHCl_3$).
Melting point: 125°-127.5° C.

C. Preparation of methyl (retinyl 2,3,4-tri-O-acetyl-β-D-glucopyranosid)uronate 5.0 g (12 mmol) of the aldehyde obtained as in Example 2B, 6.75 g (12 mmol) of β-ionylideneethyltriphenylphosphonium chloride were dissolved in 100 ml of $CH_2Cl_2$ under a nitrogen atmosphere, and 75 ml of water were added. The mixture was then cooled to 0° C. and, after addition of 25 ml of a 1N NaOH solution, stirred vigorously (turbine-type impeller). Reaction was complete after 15 min (TLC; toluene/EA 3:1 V/V). The organic phase was separated off, washed with water and dried over. $MgSO_4$.

Yield: 5.68 g, corresponding to 77% of theory, of cis/trans mixture. Fractionation of the mixture by chromatography on silica gel 60 with toluene/ethyl acetate 10:1 V/V as eluent yielded the cis and trans isomers with the following data:
1. cis $[\alpha]_D^{20}$: $-41.2°$ (C=1; $CHCl_3$).
2. trans $[\alpha]_D^{20}$: $-46.9°$ (C=1; $CHCl_3$).

We claim:
1. A process for preparing a retinyl glycoside of the formula I

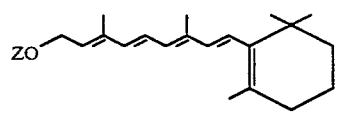

(I)

where Z is a straight-chain or branched glycosidic residue containing from 1 to 20 glycosidic units per residue, by glycosidation of a completely acylated carbohydrate or completely acylated glycosidic polymer of the formula II Z (acylated)-Y (II)

where Y is a leaving group suitable for glycosidations, in the 1-position of the carbohydrate or in the 1-position of the terminal glycoside unit, and where the H atoms of the free OH groups of the acylated glycoside or acylated glycosidic polymer have been replaced by $-CO-R_1$ where $R_1$ is alkyl of 1 to 10 carbon atoms or aralkyl, which comprises A. reacting the acylated carbohydrate or glycosidic polymer with an aldehyde-protected 4-hydroxy-2-methyl-2-buten-1-al of the formula III

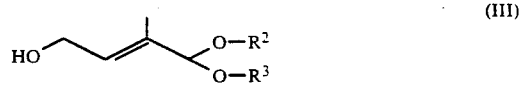

(III)

where $R^2$ and $R^3$ are each alkyl or aralkyl of up to 10 carbon atoms, or $R^2$ and $R^3$ are together ethylene or propylene, each of which can be substituted by alkyl groups of 1 to 4 carbon atoms, under the conditions suitable for glycosidations, B. eliminating the aldehyde protective group from the resulting compound of the formula IV

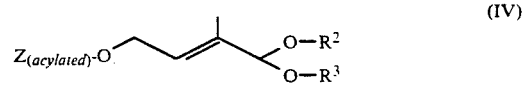

(IV)

with acid,

C. reacting the resulting aldehyde of the formula V

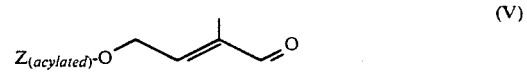

(V)

in a Wittig reaction with a β-ionylideneethyltriphenylphosphonium salt of the formula VI

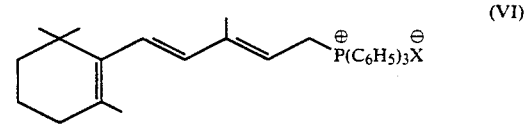

(VI)

where X is a singly charged anion, and a strong base, and

D. eliminating the acyl groups of the glycoside residue in the resulting acylated retinyl glycoside of the formula VII

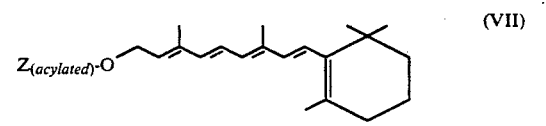

(VII)

2. A process for preparing a retinyl glycoside of the formula I as defined in claim 1, wherein the completely acylated carbohydrate or glycosidic polymer of the formula II Z (acylated)-Y (II)

is one in which Y is Cl or Br.

3. A process as defined in claim 1 for preparing a retinyl glycoside of the formula Ia

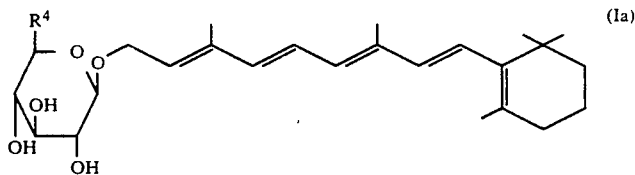

where $R^4$ is $-CH_2-OH$, $-COOH$ or $-COOCH_3$, which comprises

A. reacting an acylated glycoside of the formula IIa

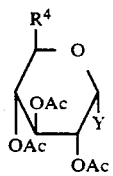

where $R^4$ is $-CH_2-OCOCH_3$ or $-COOCH_3$, Y is as defined in claim 1 and Ac is acyl of 1 to 11 carbon atoms, or arylcarbonyl, with an acetal of 4-hydroxy-2-methyl-2-buten-1-al of the formula III, B. eliminating the aldehyde protective group from the resulting compound of the formula IVa

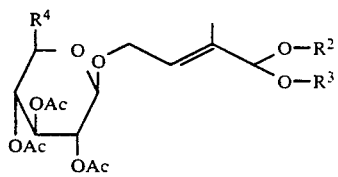

where $R^2$, $R^3$ and Ac are as defined in claim 1, and $R^4$ is $-CH_2-OCOCH_3$ or $-COOCH_3$, C. reacting the resulting aldehyde of the formula Va

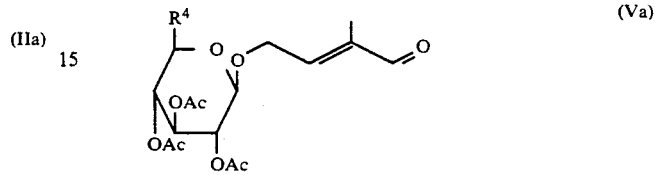

with a β-ionylideneethyltriphenylphosphonium salt of the formula VI and

D. eliminating the protective groups in the glycosidic residue of the resulting retinyl glycoside of the formula VIIa

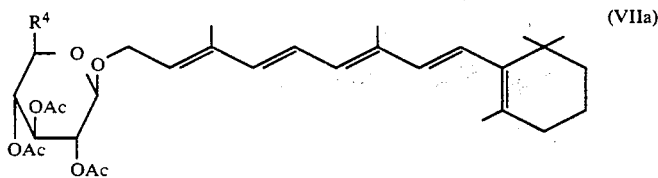

4. 1-O-(2'-Methyl-2'-buten-4'-yl-1'-al-neopentyl glycol acetal)-2,3,4,6-tetra-O-acetyl-β-D-glucopyranoside.

5. Methyl [1-O-(2'-methyl-2'-buten-4'-yl-1'-al neopentyl glycol acetal)-2,3,4-tri-O-acetyl-β-D-glucopyranosid]-uronate.

6. 1-O-(2'-Methyl-2'-buten-4'-yl-1'-al)-2,3,4,6-tetra-O-acetyl-β-D-glucopyranoside.

7. Methyl [1-O-(2'-methyl-2'-buten-4'-yl-1'-al)-2,3,4-tri-O-acetyl-β-D-gluco-pyranosid]-uronate.

8. The process of claim 1, wherein in step A the glycosidation is carried out in the presence of silver salts, $Hg(CN)_2$, $HgBr_2$ or Lewis acids in aprotic solvents.

* * * * *